(12) United States Patent
Furst et al.

(10) Patent No.: US 9,436,277 B2
(45) Date of Patent: Sep. 6, 2016

(54) SYSTEM AND METHOD FOR PRODUCING COMPUTER CONTROL SIGNALS FROM BREATH ATTRIBUTES

(71) Applicant: Xerox Corporation, Norwalk, CT (US)

(72) Inventors: Michael R. Furst, Penfield, NY (US);
Edgar A. Bernal, Webster, NY (US);
Robert P. Loce, Webster, NY (US);
Lalit K. Mestha, Fairport, NY (US)

(73) Assignee: Xerox Corporation, Norwalk, CT (US)

( * ) Notice: Subject to any disclaimer, the term of this patent is extended or adjusted under 35 U.S.C. 154(b) by 52 days.

(21) Appl. No.: 14/257,393

(22) Filed: Apr. 21, 2014

(65) Prior Publication Data
US 2015/0301590 A1    Oct. 22, 2015

(51) Int. Cl.
| | |
|---|---|
| G06F 3/01 | (2006.01) |
| A61B 5/113 | (2006.01) |
| A61B 5/08 | (2006.01) |
| G06F 3/00 | (2006.01) |
| A61B 5/00 | (2006.01) |
| A61B 5/087 | (2006.01) |

(52) U.S. Cl.
CPC ............. *G06F 3/011* (2013.01); *A61B 5/0077* (2013.01); *A61B 5/08* (2013.01); *A61B 5/087* (2013.01); *A61B 5/0816* (2013.01); *A61B 5/1135* (2013.01); *A61B 5/7485* (2013.01); *G06F 3/005* (2013.01); *A61B 2560/0223* (2013.01); *A61B 2576/00* (2013.01)

(58) Field of Classification Search
CPC ...... G06F 3/011; G06F 3/005; G06T 7/0051; G06T 7/2093; G06T 7/0012; G06T 2207/10028; G06T 2207/30196; G06T 2576/00; G06T 2560/0223; A61B 5/087; A61B 5/0816; A61B 5/0077; A61B 5/7485; A61B 2560/0223; A61B 2576/00; A61B 5/1135; A61B 5/08

See application file for complete search history.

(56) References Cited

U.S. PATENT DOCUMENTS

| | | | |
|---|---|---|---|
| 2004/0046736 A1* | 3/2004 | Pryor et al. .................... | 345/156 |
| 2010/0194741 A1* | 8/2010 | Finocchio ...................... | 345/419 |
| 2010/0195869 A1* | 8/2010 | Geiss .............................. | 382/103 |
| 2011/0080336 A1* | 4/2011 | Leyvand et al. ............... | 345/156 |
| 2011/0210915 A1* | 9/2011 | Shotton .............. | G06K 9/00369 345/157 |
| 2012/0075462 A1* | 3/2012 | Chen et al. ..................... | 345/156 |
| 2012/0257797 A1* | 10/2012 | Leyvand et al. ............... | 382/118 |
| 2013/0053718 A1* | 2/2013 | Hung et al. .................... | 600/534 |

(Continued)

FOREIGN PATENT DOCUMENTS

BE    WO 2014001058 A1 *    1/2014    ........... G06T 7/0042

OTHER PUBLICATIONS

Yu et al., Noncontact Respiratory Measurement of Volume Change Using Depth Camera, Aug. 28-Sep. 1, 34th Annual International Conference of the IEEE EMBS, whole document.*

(Continued)

*Primary Examiner* — Nalini Mummalaneni
*Assistant Examiner* — Ivelisse Martinez Quiles
(74) *Attorney, Agent, or Firm* — Fay Sharpe LLP (57) ABSTRACT

A method for computing output using a non-contact (invisible) input signal includes acquiring depth data of a scene captured by a depth-capable sensor. The method includes generating a temporal series of depth maps corresponding to the depth data. The method includes generating at least one volumetric attribute from the depth data. The method includes generating an output based on the volumetric attribute to control actions.

22 Claims, 4 Drawing Sheets

(56) References Cited

U.S. PATENT DOCUMENTS

| | | | |
|---|---|---|---|
| 2013/0278504 A1* | 10/2013 | Tong | G06F 3/017 345/158 |
| 2013/0324876 A1 | 12/2013 | Bernal | |
| 2014/0037166 A1* | 2/2014 | De Haan et al. | 382/128 |
| 2014/0094307 A1* | 4/2014 | Doolittle et al. | 345/156 |
| 2015/0154453 A1* | 6/2015 | Wilf | G06K 9/00711 382/103 |

OTHER PUBLICATIONS

U.S. Appl. No. 13/905,788, entitled "Estimating a Pose of a Camera for Volume Estimation", filed May 30, 2013, by Wencheng Wu et al.

U.S. Appl. No. 13/920,241, entitled "Handheld Cellular Apparatus for Volume Estimation", filed Jun. 18, 2013, by Wencheng Wu et al.

Dalal et al., "Histograms of Oriented Gradients for Human Detection", Proc. of 2005 Int'l Conf. on Computer Vision & Pattern Recognition, 2005, 8 pgs.

Plagemann et al., "Real-Time Identification and Localization of Body Parts from Depth Images", 2010 IEEE Int'l Conf. on Robotoics and Automation, Anchorage Convention District, May 3-8, 2010, Anchorage, Alaska, pp. 3108-3113.

Xia et al., "Human Detection Using Depth Information by Kinect", Computer Vision and Pattern Recognition Workshops, 2011, pp. 15-22.

U.S. Appl. No. 14/223,402, entitled "Non-Contact Monitoring of Spatio-Temporal Respiratory Mechanics via Depth Sensing", filed Mar. 24, 2014, by Bernal et al.

\* cited by examiner

SYSTEM AND METHOD FOR PRODUCING COMPUTER CONTROL SIGNALS FROM BREATH ATTRIBUTES

BACKGROUND

The disclosure relates to a system and method for using an invisible interface for receiving a non-contact input signal, such as a non-articulated change in shape, for controlling a device. Although the present system is discussed in the context of a gaming application, the embodiments discussed herein are amenable to other scenarios that operate using a human-machine interface.

The Human-Computer Interface (HCI) is a communication paradigm between the human user and the computer. The user essentially operates and controls the computer or device through various inputs, made at the HCI, which are provided as control signals transmitted to a computer processor for generating a particular action. Conventional HCIs accept input via mechanical contact devices, such as, computer keyboards, mice, and touch screens, etc. Assistive technology includes assistive (and adaptive and rehabilitative) devices that enable people with disabilities to perform tasks using an alternative input device (alternative HCI), such as electronic pointing devices, joysticks, and trackballs, etc. For example, Sip-and-Puff technology is a type of assistive technology that enables a user to control peripheral devices using mouth-controlled input, such as air pressure, particularly by inhaling or exhaling on a straw, tube, or wand. Also known is a non-contact (pointing) input device which responds to the volume—associated with a pressure—of the user's controlled breathing signals directed into a microphone. Similarly, a breath signal controller uses a sensor to measure pressure resulting from a user inhaling and exhaling air. Regardless of the attribute being sensed and/or measured, technology has not advanced greatly toward applying the breath pressure and/or attribute as an input signal to a controller for controlling a device.

Recent developments in the gaming industry enable detected movements to be applied as an alternative form of input. Motion-input devices determine relative motion (via accelerometers), absolute motion (via body or controller localization) and body posture (via image analyses and depth maps) parameters, which can be used to provide input signals to a gaming console.

New approaches to sensing and applying attributes as device inputs can provide useful options to a number of industries, including the healthcare and gaming industries. A Natural User Interface ("NUI") is an interface that is effectively invisible and relies on the user—as opposed to an artificial interface or control device—interacting with the technology. In other words, the user (i.e., the human body) is the interface, and the input signals applied to a processor controlling the device are associated with observed (intentional or unintentional) actions of the user. NUIs are characterized by shallow learning curves where the interface requires learning, but the user generally experiences a quick transition from novice to expert.

Neither the motion-input devices nor the human-machine interface devices are known to apply non-articulated changes in shape as an input attribute for controlling signals to a controller of the device. A NUI (i.e., an invisible interface) is desired to exploit gestures in body motion for controlling a device.

INCORPORATION BY REFERENCE

Dalal, et al., *Histograms of Oriented Gradients for Human Detection*, International Conference on Computer Vision & Pattern Recognition 2005 is fully incorporated herein.

Xia, et al., *Human Detection Using Depth Information by Kinect*, Computer Vision and Pattern Recognition Workshops 2011 is fully incorporated herein.

Plagemann, et al., in *Real-time Identification and Localization of Body Parts from Depth Images*, International Conference on Robotics and Automation 2010, which is fully incorporated herein.

The disclosure of co-pending and commonly assigned U.S. Publication No. 2013/0324876 entitled "Processing a Video for Tidal Chest Volume Estimation", filed Jun. 1, 2012, by Edgar A. Bernal, et al., the content of which is totally incorporated herein by reference.

The disclosure of co-pending and commonly assigned U.S. application Ser. No. 14/223,402, entitled "Non-contact monitoring of spatio-temporal respiratory mechanics via depth sensing," filed Mar. 24, 2014 by, E. Bernal, et al., the content of which is totally incorporated herein by reference.

The disclosure of co-pending and commonly assigned U.S. application Ser. No. 13/905,788, entitled "Estimating a Pose of a Camera for Volume Estimation," filed May 30, 2013 by, Wencheng Wu, et al., the content of which is totally incorporated herein by reference.

The disclosure of co-pending and commonly assigned U.S. application Ser. No. 13/920,241, entitled "Handheld Cellular Apparatus for Volume Estimation," filed Jun. 18, 2013 by, Wencheng Wu, et al., the content of which is totally incorporated herein by reference.

BRIEF DESCRIPTION

The disclosure relates to a method for computing output using a non-contact (invisible) input signal. The method includes acquiring depth data of a scene captured by a depth-capable sensor. The method includes generating a temporal series of depth maps corresponding to the depth data. The method includes generating at least one volumetric attribute based on the depth data determined from the series of depth maps. The method includes generating an output based on the volumetric attribute.

Another embodiment of the disclosure relates to a system for computing output using a non-contact input signal. The system comprises a non-contact interface detection device including a memory and a processor in communication with the processor configured to acquire depth data of a scene from a depth-capable sensor and generate a temporal series of depth maps. The processor is further configured to localize a subject using the depth data. The processor is further configured to generate at least one volumetric attribute based on the depth data determined from the series of depth maps. The processor is further configured to communicate an output based on the volumetric attribute.

DETAILED DESCRIPTION

The present disclosure relates to a method and a system that acquires volumetric data and applies the data as an input control signal for operating a processing unit and/or controlling a device.

Figure 1:
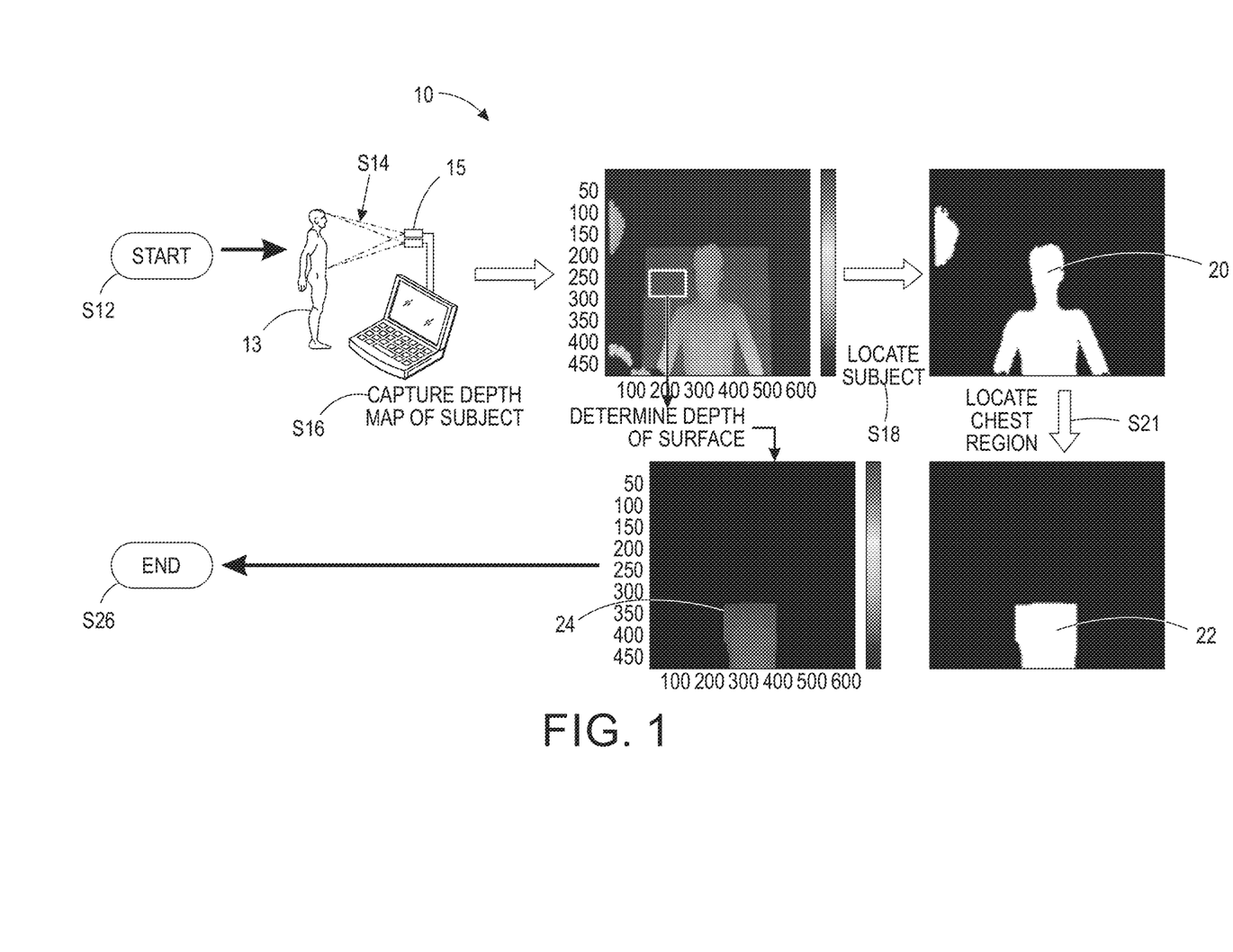
FIG. 1 is a schematic flow diagram that visually illustrates an overview of a method for controlling a device using non-articulated motion data, such as a change in shape and/or volumetric data, according to one exemplary embodiment.

FIG. 1 is a schematic flow diagram that visually illustrates an overview of a method 10 for controlling a device using non-articulated motion data, such as a change in shape and/or volumetric data, according to one exemplary embodiment. The method starts at S12. At S14, the subject—being a human user 13 in FIG. 1—is monitored by the sensor 15, which is an image capture device in the illustrated embodiment. The sensor transmits the captured data to a depth-capable sensing module, which converts each image into a depth map at S16. The depth-capable sensing module transmits the depth map(s) to a subject localization module, which performs a localization on the depth map to detect and/or locate the subject within the depth map at S18. Once the subject is located, the location of the pixels 20 associated with the subject are transmitted to a ROI localization module. In the illustrated embodiment, the information identifying the location of the pixels can be transmitted in the form of a binary image of the subject, where any pixels not associated with the subject are turned 'off' or are considered as not being relevant. The ROI localization module segments the image of the subject at S21 to identify the pixels associated with a specific body part 22, i.e., a region of interest associated with the attribute being analyzed. The information regarding these pixels (within the depth map) is transmitted to the control signal determination module, which analyzes the attribute. For example, where the region of interest is the chest region, pixels in the depth map 24 are analyzed to determine changes in the chest region. In particular, the chest walls may raise and fall as the subject inhales and exhales, respectively. The chest wall expands more for deeper breaths and less for shallower breaths. The images are acquired and processed in a succession of image frames, producing a temporal sequence of depth maps, which are analyzed to determine shape and volume changes over time. The control signal determination module converts the attribute (e.g., change in shape of chest region) into an input signal for applying to a computer processor and/or controlling an output device. The method ends at S26.

Figure 2:
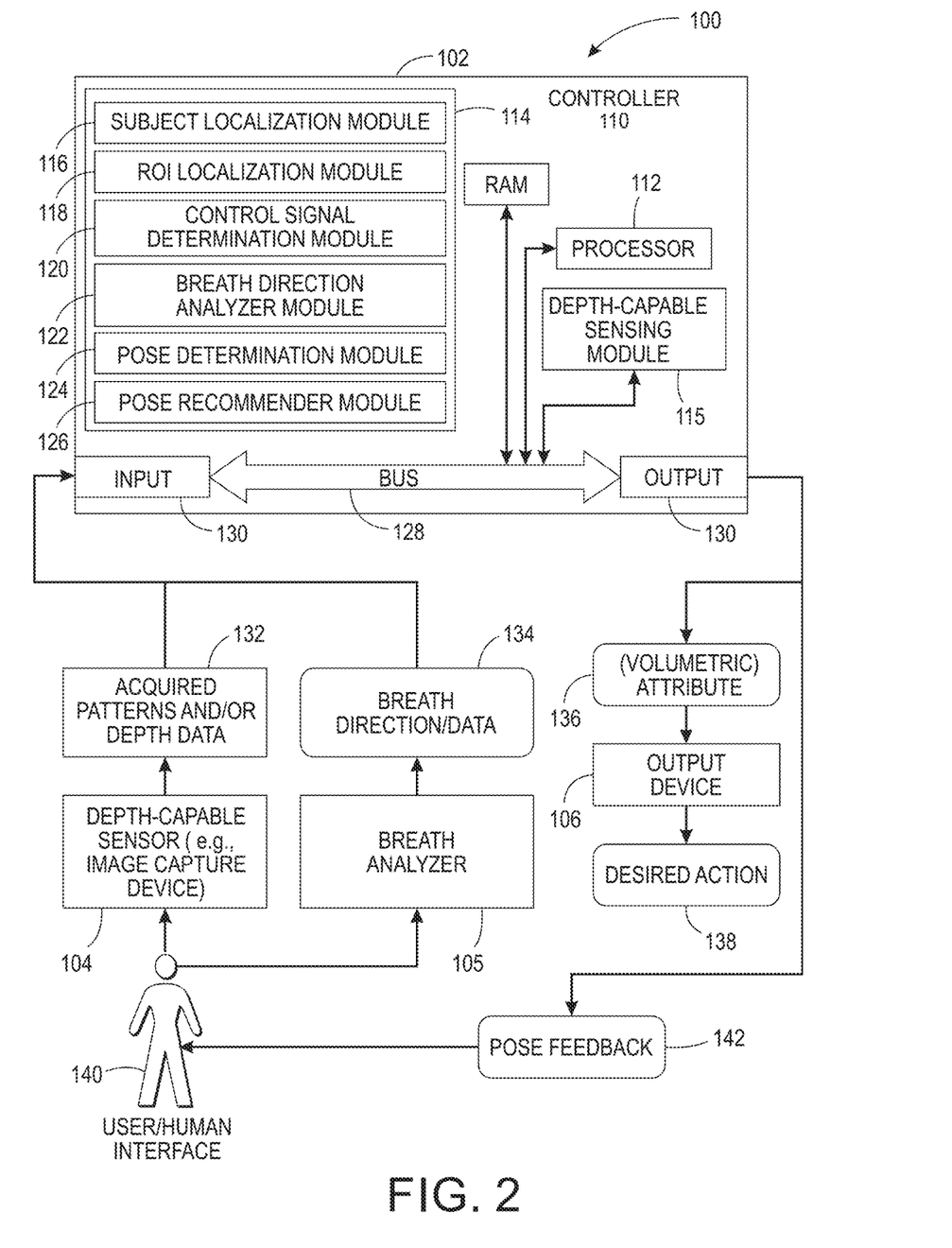
FIG. 2 is a schematic illustration of a system for controlling a device using non-articulated motion data according to one exemplary embodiment.

FIG. 2 is a schematic illustration of a system 100 for controlling a device using non-articulated motion data, such as a change in shape and/or volumetric data, according to one exemplary embodiment. The system includes a depth data analysis device 102, a depth-capable sensor 104, and an output device 106, which may be linked together by communication links, referred to herein as a network. In one embodiment, the system 100 may be in further communication with breath analyzer/sensor device 105 or additional sensors (not shown). These components are described in greater detail below.

The device 102 illustrated in FIG. 2 includes a controller 110 that is part of or associated with the device. The exemplary controller 110 is adapted for controlling an analysis of data, such as depth data 132 and/or breath direction data 134 received by the system 100 by generating at least one attribute 136 based on the received data and applying the attribute to the output device 106 for controlling a desired action 138.

The controller 110 includes a processor 112, which is configured to control the overall operation of the device 102 by execution of processing instructions that are stored in a computation module 114 including a memory connected to the processor 112.

The memory of the computation module 114 may represent any type of tangible computer readable medium such as random access memory (RAM), read only memory (ROM), magnetic disk or tape, optical disk, flash memory, or holographic memory. In one embodiment, the memory comprises a combination of random access memory and read only memory. The digital processor 112 can be variously embodied, such as by a single-core processor, a dual-core processor (or more generally by a multiple-core processor), a digital processor and cooperating math coprocessor, a digital controller, or the like. The digital processor, in addition to controlling the operation of the determination device 102, executes instructions stored in memory for performing the parts of the method outlined in FIG. 3. In some embodiments, the processor 112 and memory may be combined in a single chip.

The depth data analysis device 102 may be embodied in a networked device, such as the sensor 104, although it is also contemplated that the device 102 may be located elsewhere on a network to which the system 100 is connected, such as on a central server, a networked computer, or the like, or distributed throughout the network or otherwise accessible thereto. The phases disclosed herein are performed by the processor 112 according to the instructions contained in the memory.

In particular, the computation module 114 can receive depth-data 132 output from the depth-capable sensor 104. Alternatively, the depth data analysis device 102 can include a depth-capable sensing module 115, which can receive signals from the depth-capable sensor 104 and convert the signals to the depth data. In this latter embodiment, the depth-capable sensing module 115 contains algorithms that convert acquired patterns (i.e., the signals or images) to the depth data. The depth-capable sensing module 115 then transmits the computed depth-data to the computation module 114, which processes the depth-data to generate a volumetric attribute using the following modules: a (subject) localization module 116, which determines coordinates describing a location of a user(s) in a scene of interest; a region of interest (ROI) localization module 118, which locates a select region/part of the subject for which volumetric changes (changes in motion) can be computed; a control signal determination module 120, which continuously estimates an input control signal through an analysis of the acquired depth data stream and forwards it to the output device; a breath direction analysis module (analyzer) 122, which determines an orientation of a face of the subject and estimates a direction of inhale and exhale air flow created by breathing; a pose determination module 124, which determines one of an optimal pose of the subject and an orientation of the subject and provides the one of the optimal pose and orientation to the output device as the output; and a pose recommender module 126, which provides feedback to the subject/interface 140 as to how to modify its breathing to maximize a quality of the acquired control signal. The modules 116-126 are later described with reference to the exemplary method.

The software modules as used herein, are intended to encompass any collection or set of instructions executable by the device 102 or other digital system so as to configure the computer or other digital system to perform the task that is the intent of the software. The term "software" as used herein is intended to encompass such instructions stored in storage medium such as RAM, a hard disk, optical disk, or so forth, and is also intended to encompass so-called "firmware" that is software stored on a ROM or so forth. Such software may be organized in various ways, and may include software components organized as libraries, Internet-based programs stored on a remote server or so forth, source code, interpretive code, object code, directly executable code, and so forth. It is contemplated that the software may invoke system-level code or calls to other software residing on a server (not shown) or other location to perform certain functions. The various components of the device 102 may be all connected by a bus 128.

With continued reference to FIG. 2, the device 102 also includes one or more communication interfaces 130, such as network interfaces, for communicating with external devices. The communication interfaces 130 may include, for example, a modem, a router, a cable, and and/or Ethernet port, etc. The communication interfaces 130 are adapted to receive sensor (depth/breath/direction) data 132, 134 as input.

The device 102 may include one or more special purpose or general purpose computing devices, such as a server computer, or any other computing device capable of executing instructions for performing the exemplary method.

FIG. 2 further illustrates the device 102 connected to at least one sensor 104, 105. A depth-capable (e.g., an RGBD) sensor 104 measures visual and depth data (or changes in such data) from the scene of interest (such as, a subject 140) and transmits the sensed data 132 to the device 102. Similarly, a breath sensor 105 measures a direction of airflow created by breathing of the subject 140 and transmits the sensed data 134 to the device 102. In one embodiment, the sensor 104 can be a part of a camera/image capture device adapted to capture the subject breathing, where the depth data and/or changes in the depth data can be determined by analyzing the depth data across a series of the images received from the camera/image capture device. Low-cost, depth-capable sensing devices are readily available in the market. The sensor 104 can include an active stereo system, typically comprising an RGB camera (and optionally an Near-InfraRed (NIR) camera) and a structured illumination projector (e.g., Microsoft Kinect® Sensor). Alternatively, the sensor 104 can include a passive stereo system or traditional stereo camera consisting of two or more RGB cameras separated by a known distance or baseline. In other words, the sensor can include a first image capture device located at a first position and capturing a first view of the scene and a second image capture device located at a second position separated a predetermined distance from the first image capture device and capturing a second view of the scene, which is offset a predetermined degree from the first view of the scene. In yet another embodiment, the sensor can include a time of flight system, which measures the time of flight of a light signal between a light source in sensor 104 and the subject 140 for each point of the image using a laser or light pulse. In another embodiment, video/imaging data (for detecting and analyzing motion data) may be input from any suitable source, such as a workstation, a database, a memory storage device, such as a disk, or the like.

With continued reference to FIG. 2, the sensed depth and/or breathing direction data 132, 134 undergoes processing by the analysis device 102 to output an attribute 136 representing an input signal (instruction) for applying to the output/peripheral device 106. The system 100 is operative to apply the attribute 136 to an algorithm for outputting a desired action 138. The output/peripheral device 106 can include, in contemplated embodiments, a household device or gaming console. The output device 106 can include hardware for providing a virtual environment and/or status that is adaptable to the input control signal. This status can be provided as at least one of a graphical, visual, and audio signal. Accordingly, the output device can include a graphical user interface including a display. Other examples of contemplated output devices include speakers, printers, and e-ink devices, etc.

Figure 3:
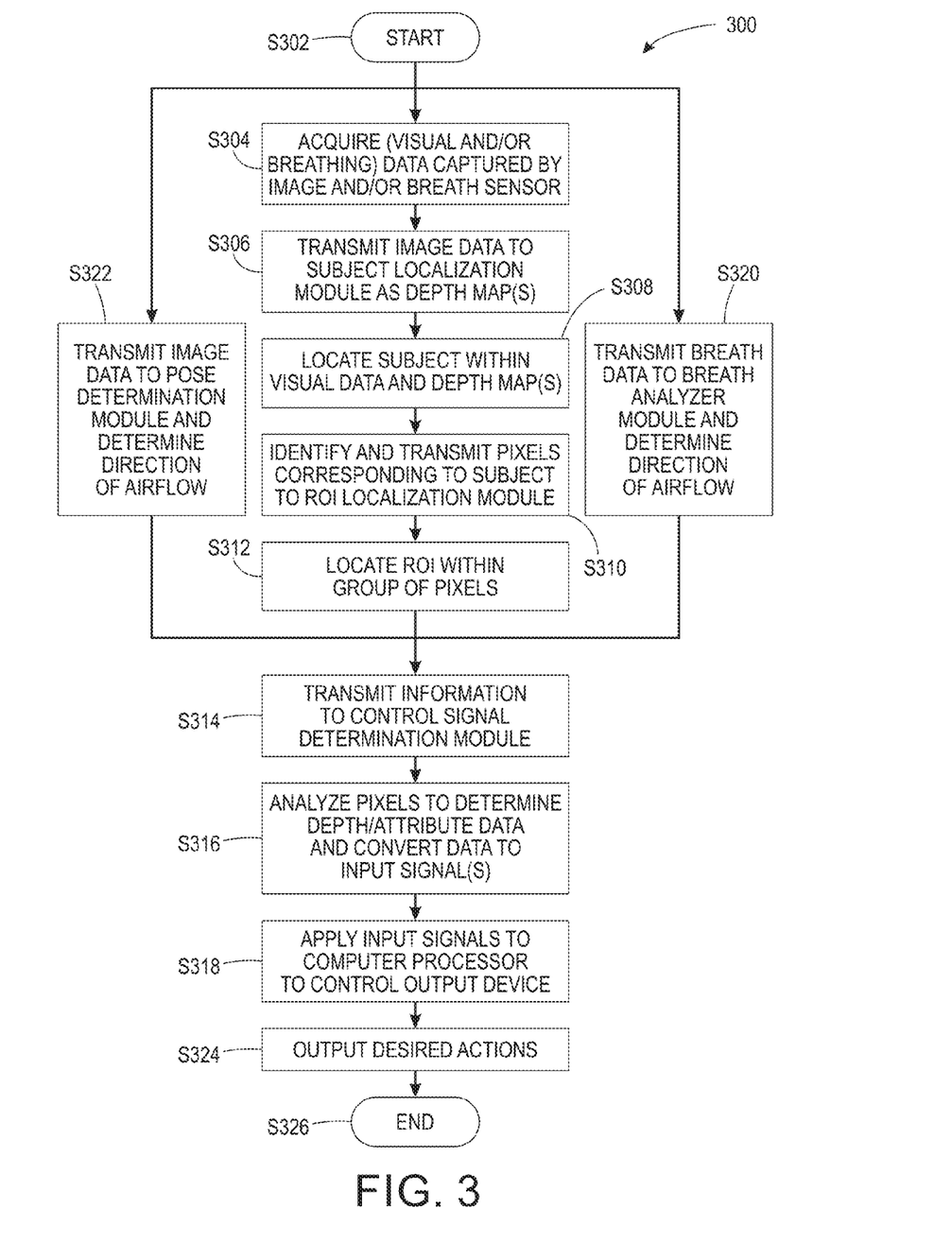
FIG. 3 is a flowchart of a method for converting data received from an invisible interface into a non-contact input signal for controlling a device.

Now referring to FIG. 3, a flowchart is shown illustrating a method 300 for converting data received from an invisible interface into a non-contact input signal for controlling a device. The method starts at S302. The depth-capable sensing module 115 (and/or breath direction analyzer module 122) acquires data captured and transmitted by the sensor(s) 104, 105 monitoring a scene of interest at S304. Particularly, these modules 115, 122 receive data transmitted from the depth-capable sensor and/or breath sensor 104, 105. More specifically, the sensors 104, 105 include non-contact devices that monitor and/or capture actions of the subject, removed from the sensor device, within the scene of interest. In other words, the subject does not physically interact with the sensor. By "scene of interest", the discussed embodiment contemplates a scene including a live subject, such as a user and/or human. The subject 140 is treated by the system 100 as a light-based interface without any hardware link, where the deliberate and/or monitored actions of the subject can generate data used as input to control the output device 106. In the case of a human subject/user in the discussed embodiment, these deliberate actions can include body movements, such as torso deformations that lead to changes in volume contained in the lungs—i.e., by inhaling and exhaling.

The module 115 receives the captured data so the system 100 can compute vital statistics/information. In one embodiment, the captured (sensor/sensed) data is received in the form of image and/or video data. The module 115 can acquire data in the form of RGB data of the monitored scene. This RGB data can be received as video frames and/or images captured using an image-capture device. The images each describe a visual appearance of the scene.

In another embodiment, the captured data is in the form of measurements taken by a sensor device. Measurements acquired by the module 115 can be used by the module to determine rates of inhaling/exhaling, volume of air intake, and pressure of exhale, etc. In one embodiment, data received by breath analyzer 105 can be used to determine a direction of airflow generated during breathing (i.e., during inhales and exhales). There is no limitation made herein to the type of data being measured and/or sensed or the type of attribute being determined using the acquired data. Nor is there a limitation made herein to the type of sensor used for capturing the data.

The present disclosure proposes the use of monitored attributes of the subject as a means to generate input control signals into the computer processor 112. Regardless of the data type and/or attribute being monitored, the module 115 forwards the received data to the subject localization module 116 for further processing. In the contemplated embodiment where the sensor device is a depth-sensing device, the module 115 can transmit the data to the subject localization module 116 as a series of depth maps at S306. Furthermore, the module 115 can perform morphological operations on each depth map before transmitting it to the subject localization module 116.

Accurate subject localization is central to an operation of the system 100. In the discussed embodiment, subject localization is performed on the image and/or video frame ("visual data"). Mainly, at S308 the subject localization module 116 detects and/or locates the subject within the transmitted visual data, or more particularly within the received depth map. Any conventional computer vision technique can be performed on the visual data for detecting the subject. For example, one contemplated technique for detecting a human on RGB data is disclosed by Dalal, et al., in *Histograms of Oriented Gradients for Human Detection*, International Conference on Computer Vision & Pattern Recognition, dated 2005, which is fully incorporated herein. Another contemplated technique for detecting a human on RGBD data is disclosed by Xia, et al., in *Human Detection Using Depth Information by Kinect*, Computer Vision and Pattern Recognition Workshops 2011, which is fully incorporated herein.

Mainly, the localization module 116 identifies pixels corresponding to the subject being monitored in the scene of interest. For visual data, depending on the computational complexity of the localization algorithm used and a video frame rate of the image capture device monitoring the scene of interest, the module 116 can perform the localization on a frame-by-frame basis or on every predetermined number of frames. For embodiments that perform the localization on every predetermined number of frames, a tracking algorithm can be performed to track a location of the subject across the frames. In other words, once the subject is detected in a first frame, the subject is tracked across the series of frames so that its localization is maintained for the next, predetermined frame undergoing the localization operation.

The module 116 identifies pixels corresponding to the subject at S310 by determining a depth of the surface in the depth map. The determined pixels corresponding to the subject are then transmitted to the region of interest (ROI) localization module 118. In one embodiment, these pixels are included in a binary (or similar classification) image of the subject being transmitted to the ROI localization module 118. The module 118 generally locates a region of interest within the group of pixels representing the object at S312.

The "ROI" refers to a select region of the subject for which the attribute is being analyzed. While the choice for a target ROI depends on the specific application, the ROI will typically be a body part or a collection of body parts. For example, in an embodiment where the attribute is a non-articulated change in shape representing air volume, the ROI can include the diaphragm or torso regions of the subject.

The disclosure contemplates that any conventional approach, such as that used for MS Kinect® devices, for detecting and/or locating a body part can be performed on the pixels received from the subject localization module 116. One contemplated approach is disclosed by Plagemann, et al., in *Real-time Identification and Localization of Body Parts from Depth Images*, International Conference on Robotics and Automation 2010, which is fully incorporated herein. These systems are capable of identifying twenty-five (25) or more skeleton joints from up to six (6) simultaneous people being monitored in a scene of interest. Examples of joints can include head, neck, shoulders, elbows, abdomen, wrists, hands, hips, knees, ankles and feet, etc. In the contemplated embodiment, the ROI localization module 118 has knowledge of a location of these different body joints.

The present embodiment contemplates monitoring volumetric data as the attribute to be converted and applied as the input signal for the computer processor. Accordingly, the ROI generally can include the chest and abdominal regions of the subject. The ROI localization module 118 segments the image (pixels) representing the subject to locate the chest and abdominal regions. Any known computationally efficient segmentation algorithm is contemplated for performing the operation. More specifically, the module 118 identifies the pixels specifically associated with the region of interest, being the chest and abdominal regions in the illustrated embodiment. The information regarding a location of the ROI pixels (in both the depth map and the generated binary image) is transmitted to the control signal determination module 120 at S314, which analyzes attributes of the ROI and converts them into control signals.

The control signal determination module 120 analyzes the pixels to determine the attribute (e.g., extracted from depth data) of the ROI and converts the attributes into control signals at S316. More specifically, the identified pixels in the depth maps, corresponding to the ROI, are analyzed to identify and/or determine the depth-data. Depth-data or a "depth map" is an image or image channel that contains information relating to the distance of the surfaces of scene objects from a viewpoint. In another contemplated embodiment, the module 120 acquires the information (s.a., the chest/abdominal position) and can compute from the depth-data, changes (s.a., the deformation) in the volume, pose, orientation of this body region, etc.

In one embodiment, the module 120 processes at least two depth maps (each corresponding to a frame in the video data) for determining the changes in depth-data between frames. At this point, the amount of change is treated as the attribute.

While the contemplated embodiment does not require a knowledge of the volume in absolute, real-world coordinates (s.a., in milliliters (mL) and cubic centimeters ($cm^3$)), a knowledge of relative volumes within a subject or between multiple users is contemplated for use. Furthermore, embodiments are contemplated for calibrating the volumetric data. The present disclosure can implement any known calibration technique for calibrating the volume. For example, one calibration technique using an RGBD sensor is provided in co-pending and commonly assigned U.S. Publication No. 2013/0324876 entitled "Processing a Video for Tidal Chest Volume Estimation", filed Jun. 1, 2012, by Edgar A. Bernal, et al., which is totally incorporated herein by reference. Another calibration technique using an RGBD sensor is provided in co-pending and commonly assigned U.S. application Ser. No. 13/905,788, entitled "Estimating a Pose of a Camera for Volume Estimation," filed May 30, 2013 by Wencheng Wu, et al., which is totally incorporated herein by reference.

Figure 4:
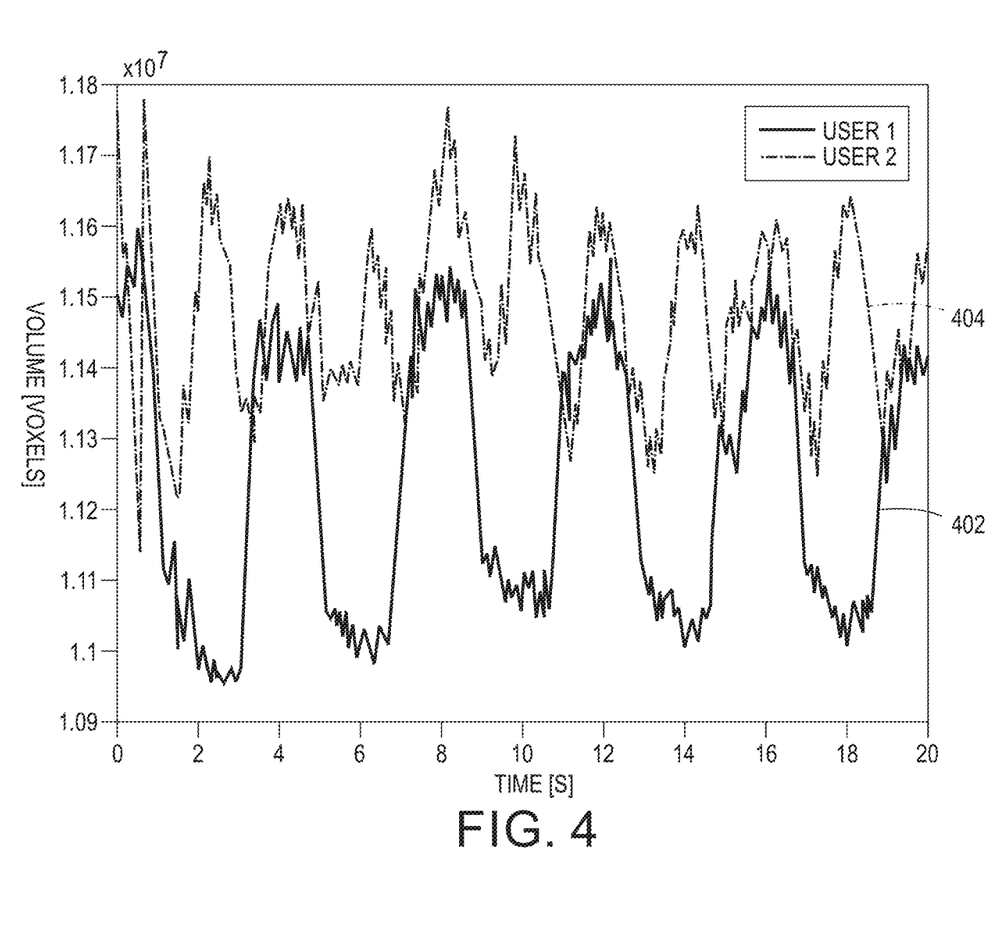
FIG. 4 is a chart showing temporal volumetric curves of chest and abdominal area (ROI) for two different subjects.

One embodiment of the disclosure applies the volumetric attributes of the ROI as input control signals that enable the subject-user to interact with a computer and/or output device at S318. Examples of volumetric attributes can include amplitude of the change in volume in a predetermined time interval and the rate of change of the volume. For example, FIG. 4 is a chart showing temporal volumetric curves of chest and abdominal area (ROI) for two different subjects, for comparison. More specifically, FIG. 4 shows a first plot 402 associated with a first subject taking deep breaths and a second plot 404 associated with a second subject taking shallow breaths relative to the breathing of the first subject. The plots 402, 404 also show that the subjects are breathing at different rates. The first plot 402 shows that the breathing pattern of the first subject is at a slower rate than the second plot 404 (second subject).

One approach contemplated for computing the volumetric data is disclosed in co-pending and commonly assigned U.S. Publication No. 2013/0324876 entitled "Processing a Video for Tidal Chest Volume Estimation", filed Jun. 1, 2012, by Edgar A. Bernal, et al., which is totally incorporated herein by reference.

Next, the module 120 computes a control signal from the plot. In the illustrated example, a separate control signal is generated for each subject/plot. For the example plots, the control signals can be derived from attributes selected from a group consisting of, for example, an estimated respiration rate, an estimated respiration volume, and a combination thereof.

Another example of input that can be used as the control signal can include a direction of airflow generated during breathing (i.e., during inhales and exhales). As mentioned supra, the breath sensor/analyzer 105 can capture and transmit data to the breath direction analyzer module 122, which can analyze the data to determine the direction of airflow at S320. Alternatively, the image capture device 104 can transmit the captured visual data to the pose determination module 124, which can analyze the select frame and/or depth map to determine the direction. Alternatively, after the ROI localization module 118 segments the image (pixels) representing the subject in the image data and/or depth maps, it can locate the face and/or head regions. Alternatively, as mentioned supra, the ROI localization module 118 contains knowledge about a location of multiple skeleton joints. The module 118 can also provide locations of particular joints to the pose determination module 124.

The information regarding a location of these regions is transmitted to the pose determination module 124, which determines a direction of breathing using any conventional pose estimation technique at S322. In one embodiment, this direction can be determined by simply identifying a direction a front of the head (of the subject) is facing by, for example, identifying a nose region. The direction can be manipulated by the subject, which can control the stream of air flowing through an opening created by the subject's lips. The subject can moderate the left-or-right direction of airflow by pursing its lips and blowing the air out of the desired side of its mouth. The module 124 can analyze the visual images and/or depth maps to determine this direction.

The embodiments herein contemplate that the direction of airflow determined by the pose determination module 124 can be used in combination with a different attribute, such as the estimated volume and/or change in volume determined by the control signal determination module 120 to generate a two-dimensional signal to input into the computer processor.

The control signal is applied to the computer processor to control actions of the output device 106 at S318. In the illustrated embodiment, the output device is used to visually communicate a status of the virtual environment to the user. This status can be provided as at least one of a graphical, visual, and audio signal, but there is no limitation made herein to the type of signal and/or output used. Accordingly, the output device includes the corresponding hardware for providing the signals and/or desired actions at S324, such as a graphical user interface including a display. The specific characteristics of the virtual environment can be based on the particular computer application. Example computer applications may include virtual reality, gaming, e-learning and communication settings, etc., but the teachings are amenable to other settings. The conditions of the virtual environment are affected by the input control signal generated by the control signal determination module 120.

In one contemplated embodiment, the system 100 can further provide recommendations for improving a quality of the data being captured for providing a more robust input signal. For example, in an embodiment where the input control data is determined from volumetric data, this quality can be affected by multiple factors including, inter alia, pose and occlusions (caused, for example, by a body extremity, etc.). The pose recommendation module 126 can provide feedback to the user regarding optimal body positions for the specific computer applications. For example, the module 126 can output a suggestion that the subject stand facing a particular direction relative to the sensor device 132. One orientation, such as a frontal view, can result in more robust volumetric data being collected. In another example, the module 126 can suggest the subject change orientation to avoid an occlusion. The method ends at S326.

Further embodiments contemplate performing calibration techniques, for example, to determine a best operational region for given users whose volumetric characteristics may differ significantly relative to one another. For example, young children (as subjects) have significantly smaller lung capacities than adults. Initialization and calibration techniques can easily be developed for each user. In this manner, the system can perform a set-up calibration procedure to build knowledge of a particular user's breathing capacities. In one example application, the system 100 can instruct the subject to perform a few breathing cycles of certain types. As an illustrative example only, these instructions may guide the subject to perform three (3) cycles of tidal breathing followed by one (1) cycle of forced inspiration and expiration cycle and three (3) cycles of tidal breathing again). The system 100 can analyze the breathing data captured during the cycles for determining information on the subject's particular vital capacities. Then, the system 100 can setup the output device (s.a., the gaming console) for receiving input relative subject's maximum vital capacities. As yet another example implementation, the system can interactively introduce the subject's breathing pattern in a displayed scene of the subject, thus making the scene appear as a close simulation of the actual scene.

One aspect of the present disclosure is an increase in the dimensions used as control signals for controlling a computer device.

Example Scenario

In one exemplary scenario, two virtual balloons can be displayed by the output device. The instantaneous volume of air intake by each subject can be measured and used as input to virtually inflate each of the balloons in a race to determine which subject is able to pop its balloon first. The volume can be estimated in this example from curves, which are measured by the control signal determination volume.

Although the method 100, 300 is illustrated and described above in the form of a series of acts or events, it will be appreciated that the various methods or processes of the present disclosure are not limited by the illustrated ordering of such acts or events. In this regard, except as specifically provided hereinafter, some acts or events may occur in different order and/or concurrently with other acts or events apart from those illustrated and described herein in accordance with the disclosure. It is further noted that not all illustrated steps may be required to implement a process or method in accordance with the present disclosure, and one or more such acts may be combined. The illustrated methods and other methods of the disclosure may be implemented in hardware, software, or combinations thereof, in order to provide the control functionality described herein, and may be employed in any system including but not limited to the above illustrated system 100, wherein the disclosure is not limited to the specific applications and embodiments illustrated and described herein.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A system for computing output using a non-contact input signal, the system comprising:
    a computer programmed to perform a method for generating an input control signal and including the operations of:
        acquiring depth data of a scene captured by a depth-capable sensor;
        generating a temporal series of depth maps corresponding to the depth data;
        generating at least one volumetric attribute based on the depth data determined from the series of depth maps, the generating including:
        for each depth map, generating a binary image of a subject detected in the each depth map,
        segmenting the binary image into regions,
        comparing pixels corresponding to a select region of interest across the temporal series of depth maps to determine a change in a shape of the region,
        associating the change in the shape with a volumetric attribute;
        determining one of an optimal pose of the subject and an optimal orientation of the subject using a breath analyzer in communication with the computer;
    providing the one of the pose and orientation to an output device as an output, and providing a pose recommendation feedback for improving a quality of the depth data; and generating an input control signal based on the volumetric attribute to enable the subject to interact with an output device.

2. The system of claim 1, wherein the computer is further operative to localize the subject by at least one of detecting and tracking the subject across the series of depth maps.

3. The system of claim 1, wherein the depth-capable sensor includes:
    a first image capture device located at a first position and capturing a first view of a scene; and,
    a second image capture device located at a second position separated a predetermined distance from the first image capture device and capturing a second view of the scene offset a predetermined degree from the first view of the scene.

4. The system of claim 1, wherein the depth-capable sensor is selected from a group consisting of:
    an active stereo device comprising a structured illumination system operative to project patterned illumination onto the subject, and an image acquisition device operative to image a reflected patterned illumination;
    a time of flight system measuring a time of flight of a light signal between a light source and the subject for each point of an image using a laser or light pulse; and,
    a combination of the above.

5. The system of claim 1 wherein the computer is further operative to generate information regarding a location of pixels corresponding to a region of interest ("ROI") within an image of the scene.

6. The system of claim 5, wherein the ROI includes at least one of a chest and abdominal area.

7. The system of claim 1, wherein the volumetric attribute is selected from a group consisting of:
    amplitude of a change in volume within a predetermined time interval;
    a rate of the change of a volume; and,
    a combination of the amplitude and the rate.

8. The system of claim 1, wherein the computer further includes the breath analyzer and is operative to:
    determine an orientation of a face of the subject and estimate a direction of inhale and exhale air flow created by breathing.

9. The system of claim 1, wherein the output includes a control signal for controlling an associated device.

10. The system of claim 1, wherein the output is a characteristic breathing pattern.

11. The system of claim 10, wherein the output device is a gaming device and the breathing pattern is introduced in a gaming scene of the subject.

12. A method for computing output using a non-contact input signal, the method including:
    acquiring depth data of a scene captured by a depth-capable sensor;
    generating a temporal series of depth maps corresponding to the depth data;
    generating at least one volumetric attribute based on the depth data determined from the series of depth maps, the generating including:
    for each depth map, generating a binary image of a subject detected in the each depth map,
    segmenting the binary image into regions,
    comparing pixels corresponding to a select region of interest across the temporal series of depth maps to determine a change in a shape of the region,
    associating the change in the shape with a volumetric attribute;
    determining one of an optimal pose of the subject and an optimal orientation of the subject using a breath analyzer in communication with the computer;
    providing the one of the pose and orientation to an output device as an output, and providing a pose recommendation feedback for improving a quality of the depth data; and generating an input control signal based on the volumetric attribute to enable the subject to interact with an output device.

13. The method of claim 12, wherein the depth-capable sensor includes:
    a first image capture device located at a first position and capturing a first view of a scene; and,
    a second image capture device located at a second position separated a predetermined distance from the first image capture device and capturing a second view of the scene offset a predetermined degree from the first view of the scene.

14. The method of claim 12, wherein the depth-capable sensor includes:
    an active stereo device comprising a structured illumination system operative to project patterned illumination onto the subject, and an image acquisition device operative to image a reflected patterned illumination.

15. The method claim 12, further comprising:
    determining pixels corresponding to a region of interest ("ROI") being monitored on a subject by the depth-capable sensor.

16. The method of claim 15, wherein the ROI includes at least one of a chest and abdominal area.

17. The method of claim 12, wherein the volumetric attribute is selected from a group consisting of:
  amplitude of a change in volume within a predetermined time interval;
  a rate of the change of a volume; and,
  a combination of the amplitude and the rate.

18. The method of claim 12, further comprising:
  determining an orientation of a face of the subject and estimating a direction of inhale and exhale air flow created by breathing activity of the subject.

19. The method of claim 12, wherein the output includes a control signal for controlling an associated device.

20. The method of claim 19, wherein the output includes a breathing pattern and the associated device is a gaming device for determining vital capacities of the subject.

21. The method of claim 12, further comprising:
  calibrating the output device by performing a breathing cycle selected from a group consisting:
    at least one tidal breathing cycle;
    a forced inspiration cycle; a forced expiration cycle; and,
    a combination of the above.

22. The method of claim 21, further comprising:
  computing maximum vital capacities of the subject using the breathing cycle.

* * * * *